(12) United States Patent
Qin et al.

(10) Patent No.: US 12,146,192 B2
(45) Date of Patent: Nov. 19, 2024

(54) USE OF microRNA (miRNA) MARKER IN PREPARATION OF PRODUCT FOR EVALUATING THERAPEUTIC EFFECT OF OLANZAPINE IN TREATMENT OF SCHIZOPHRENIA (SZ) AND KIT

(71) Applicant: SHANGHAI JIAO TONG UNIVERSITY, Shanghai (CN)

(72) Inventors: Shengying Qin, Shanghai (CN); Jing Sun, Zhenjiang (CN); Lin He, Shanghai (CN)

(73) Assignee: SHANGHAI JIAO TONG UNIVERSITY, Shanghai (CN)

( * ) Notice: Subject to any disclaimer, the term of this patent is extended or adjusted under 35 U.S.C. 154(b) by 0 days.

(21) Appl. No.: 18/025,639

(22) PCT Filed: Aug. 4, 2021

(86) PCT No.: PCT/CN2021/110486
§ 371 (c)(1),
(2) Date: Mar. 9, 2023

(87) PCT Pub. No.: WO2022/052678
PCT Pub. Date: Mar. 17, 2022

(65) Prior Publication Data
US 2023/0332233 A1 Oct. 19, 2023

(30) Foreign Application Priority Data

Sep. 9, 2020 (CN) .......................... 202010942097.3

(51) Int. Cl.
*C12Q 1/6883* (2018.01)
(52) U.S. Cl.
CPC ..... *C12Q 1/6883* (2013.01); *C12Q 2600/106* (2013.01); *C12Q 2600/158* (2013.01); *C12Q 2600/166* (2013.01); *C12Q 2600/178* (2013.01)

(58) Field of Classification Search
None
See application file for complete search history.

(56) References Cited

FOREIGN PATENT DOCUMENTS

| CN | 101985659 A | 3/2011 |
|---|---|---|
| CN | 104120172 A | 10/2014 |
| CN | 104862310 A | 8/2015 |
| CN | 105755167 A | 7/2016 |
| CN | 105950730 A | 9/2016 |
| CN | 109423519 A | 3/2019 |
| CN | 109890394 A | 6/2019 |
| CN | 111909997 A | 11/2020 |
| WO | 2019046303 A1 | 3/2019 |

OTHER PUBLICATIONS

Liu, P. et al. Hindawi J. Diabetes Res. Oct. 8, 2020. 15 pages and Supplementary Materials (2 pages) (Year: 2020).*
Pan et al. Scientific Reports. Feb. 26, 2018. 8:3624, p. 1-12 (Year: 2018).*
Jiang et al. Chinese J Reparative Reconstructive Surgery. Sep. 2019 33(9): 1174-1180, English translation included (Year: 2019).*
Liu, X. et al. Int. J COPD. 2018. 13: 1217-1228 (Year: 2018).*
Dong Li-Cai, et al., Detection of differentially expressed miRNAs in serum of patients with schizophrenia by RT-PCR, Chinese Mental Health Journal, 2015, pp. 662-666, vol. 29, No. 9.
M.M.J. Van Den Berg, et al., Circulating microRNAs as potential biomarkers for psychiatric and neurodegenerative disorders, Progress in Neurobiology, 2020, pp. 1-22, vol. 185, 101732.
Xiaoya Zhang, Discovery of microRNA as Neuregulin 1 downstream targets for the effect of olanzapine on schizophrenia-related mitochondrial dysfunction, Master's Thesis of Jiangsu University, 2021, pp. 1-70.

* cited by examiner

*Primary Examiner* — Carla J Myers
(74) *Attorney, Agent, or Firm* — Bayramoglu Law Offices LLC

(57) ABSTRACT

A use of a detection reagent for a microRNA (miRNA) marker miR-143-3p in the preparation of a product for evaluating a therapeutic effect of olanzapine in the treatment of schizophrenia (SZ) and a kit are provided. An expression level of miR-143-3p can be detected to determine a therapeutic effect of olanzapine in the treatment of SZ of a patient, and can be used as a detection or treatment index in clinical practice, which provides a theoretical basis for the mechanism research of SZ and the clinical application.

3 Claims, 2 Drawing Sheets
Specification includes a Sequence Listing.

USE OF microRNA (miRNA) MARKER IN PREPARATION OF PRODUCT FOR EVALUATING THERAPEUTIC EFFECT OF OLANZAPINE IN TREATMENT OF SCHIZOPHRENIA (SZ) AND KIT

CROSS REFERENCE TO THE RELATED APPLICATIONS

This application is the national phase entry of International Application No. PCT/CN2021/110486, filed on Aug. 4, 2021, which is based upon and claims priority to Chinese Patent Application No. 202010942097.3, filed on Sep. 9, 2020, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBDD071-PKG_Sequence_Listing.txt, created on Mar. 2, 2023, and is 1,619 bytes in size.

TECHNICAL FIELD

The present disclosure relates to the field of biotechnology, and in particular, the present disclosure relates to a use of a microRNA (miRNA) marker in the preparation of a product for evaluating a therapeutic effect of olanzapine in the treatment of schizophrenia (SZ) and a kit, and especially to a use of a peripheral blood miRNA marker miR-143-3p for evaluating a therapeutic effect of olanzapine in the treatment of SZ, a detection method, and a kit.

BACKGROUND

SZ is one of the most serious mental disorders and has the main clinical characteristics of positive symptoms such as hallucination, delusion, psychomotor excitement, and/or negative symptoms such as affective dullness, affective flattening, social withdrawal, and hypobulia. Currently, SZ is difficult to diagnose and treat, which brings extremely heavy burdens to individuals, families, and communities. Therefore, the effective prevention and treatment of SZ are extremely urgent.

Existing studies have shown that the early definitive diagnosis and timely effective treatment of SZ can significantly improve the psychological, physical, and social functions and the work performance of patients, greatly reduce medical expenses and reduce the disability rate. However, the current diagnosis of SZ still relies on the subjective evaluation of clinical symptoms of SZ, and there is a lack of an effective "gold standard" for the clinical diagnosis of SZ. Therefore, clinical misdiagnosis and mistreatment of SZ often occur. In addition, because the response characteristics of a patient to a therapeutic drug cannot be known in advance, the optimal therapeutic drug can only be found clinically through constant attempts of drug administration, which affects the therapeutic effect of SZ, reduces the medication compliance of a patient, and causes a huge waste of medical resources. Therefore, it is necessary to develop a sensitive and specific biomarker to improve the diagnostic reliability of SZ, which facilitates targeted drug intervention and clinical scientific research.

Olanzapine, also known as Zyprexa, is a second-generation atypical antipsychotic drug and has become a first-line clinical drug since it was approved for marketing in 1996. Studies have shown that olanzapine can act on NRG-1 to resist the PCP-induced decrease in the production of neuronal synapses of the prefrontal cortex (PFC). In terms of tolerability and safety, olanzapine exhibits a better therapeutic effect for SZ than conventional antipsychotic drugs but still inevitably leads to some adverse reactions. Clinical studies have shown that the long-term administration of olanzapine to a patient will induce energy metabolism syndromes such as drowsiness, weight gain, and hyperglycemia to some extent; some patients with early effective medication for a period of time will undergo positive symptoms once again, and the increase in dose cannot reverse this phenomenon, that is, olanzapine tolerance is developed. Therefore, it is necessary to develop a sensitive and specific biomarker to improve the diagnostic reliability of SZ, which facilitates targeted drug intervention and clinical scientific research.

SZ is a complicated neuropsychiatric disorder, including disturbances in neural circuits and synaptic functions. The reconstruction of delicate network structures and neuronal synapses requires the coordination of a complicated intracellular molecular signaling system. The redundancy of these networks means that many combinations of gene variants may cause system dysfunctions, which are manifested as related neurobehavioral syndromes. Recent studies have shown that post-transcriptional gene regulation and related miRNAs may be important factors in the formation of these networks. miRNAs exhibit a complicated spatial expression pattern in a mammalian brain and may regulate thousands of target genes as specific factors for intracellular gene silencing mechanisms. Because the dysregulation of miRNAs may cause pervasive changes in the network structures during development and changes in the mature brain that are highly important in the pathophysiology of SZ, miRNAs are becoming key regulators of many neurodevelopmental and neurological processes. It should be noted that these changes in miRNA expression and related mechanisms may represent new targets for drug development, and miRNA biomarkers for SZ may also provide a basis for new clinical diagnosis. This progress has great potential and highlights the importance of this research approach.

SUMMARY

In view of the defects in the prior art, an objective of the present disclosure is to provide a use of a miRNA marker in the preparation of a product for evaluating a therapeutic effect of olanzapine in the treatment of SZ and a kit.

The objective of the present disclosure is achieved through the following technical solutions:

In a first aspect of the present disclosure, a use of a miRNA marker in the preparation of a product for evaluating a therapeutic effect of olanzapine in the treatment of SZ is provided, where the miRNA marker is miR-143-3p.

A method for detecting an expression level of the miRNA marker miR-143-3p specifically includes the following steps:

Step 1: collecting blood, preparing a serum sample through centrifugation, and storing the serum sample for later use, where the serum sample includes a serum sample from peripheral blood of an SZ patient who does not respond to an olanzapine treatment and a serum sample from peripheral blood of an SZ patient who responds to an olanzapine treatment.

The serum sample is specifically obtained as follows: 3 mL of fasting venous blood is collected from each of included people in the morning and then immediately centrifuged by a horizontal centrifuge at 2,000 rpm for 8 min to allow serum separation, and a resulting supernatant is placed in a centrifuge tube and then centrifuged at 14,000 rpm and 4° C. for 10 min; and a resulting supernatant is placed in a new centrifuge tube and stored in a −80° C. refrigerator for extraction of total RNA.

Step 2: extracting total RNA.

Specific steps are as follows:

a sample is subjected to homogenization with a TRIzol™ reagent, and chloroform is added to make a homogenate separated into a transparent upper aqueous layer (including RNA), an intermediate phase, and a red lower organic layer (including DNA and a protein); RNA is precipitated from the aqueous layer with isopropanol; and the precipitated RNA is washed with ethanol to remove impurities and then resuspended with RNase-free water to obtain total RNA, and the total RNA is stored at −80° C.

Step 3: detecting a total amount of RNA with an ultra-micro spectrophotometer. Preferably, an absorbance at 260 mm is determined with the ultra-micro spectrophotometer to calculate the total amount of RNA. A method for detecting the absorbance is as follows: 2 µL of dissolved RNA is taken, and an absorbance of the dissolved RNA at 260 mm is determined with the ultra-micro spectrophotometer to calculate a yield of RNA.

Step 4: conducting reverse transcription to obtain cDNA, and detecting the cDNA through fluorescence quantification. Preferably, primers for the miRNA marker miR-143-3p used in the reverse transcription include an upstream primer of miR-143-3p, a downstream primer of miR-143-3p, and a stem-loop RT1 primer. The upstream primer of miR-143-3p has a sequence shown in SEQ ID NO: 1:

F: CGCGTGAGATGAAGCACTG;

the downstream primer of miR-143-3p has a sequence shown in SEQ ID NO: 2:

R: AGTGCAGGGTCCGAGGTATT; and the stem-loop RT1 primer has a sequence shown in SEQ ID NO: 3:

```
RT1:
GTCGTATCCAGTGCAGGGTCCGAGGTATTCGCACTGGATACGACGAGCTA.
```

Internal reference primers for detecting the expression level of the miRNA marker include an internal reference upstream primer, an internal reference downstream primer, and a stem-loop RT2 primer. An internal reference is U6 RNA. The internal reference upstream primer has a sequence shown in SEQ ID NO: 4:

F: AGAGAAGATTAGCATGGCCCCTG;

the internal reference downstream primer has a sequence shown in SEQ ID NO: 5:

R: ATCCAGTGCAGGGTCCGAGG; and the stem-loop RT2 primer has a sequence shown in SEQ ID NO: 6:

```
RT2:
GTCGTATCCAGTGCAGGGTCCGAGGTATTCGCACTGGATACGACAAAATA.
```

Preferably, the reverse transcription is conducted as follows: 2×miRNA L-RT Solution mix is thawed and thoroughly mixed, and miRNA L-RT Enzyme Mix is placed on ice for later use; 10 µL of 2×miRNA L-RT Solution mix, 1.5 µL of miRNA L-RT Enzyme Mix, 4 µg of total RNA, 1 µL of Stem-loop primer (10 µM), and the balance of RNase-Free dd $H_2O$ are added to a reaction tube pre-cooled on ice to obtain a 20 µL reaction system, and a reaction is conducted to obtain cDNA; and the cDNA is detected through fluorescence quantification. Real-time fluorescence quantitative polymerase chain reaction (PCR) of miRNA: Operations are conducted according to instructions of the SYBR Green Masrer kit, 3 replicate wells are set for each experiment, and a LightCycler 96 real-time fluorescence quantitative PCR instrument is used for detection.

Step 5: analyzing detection results by a relative quantification method, and detecting an expression level of miR-143-3p in a sample to determine whether an SZ patient responds to olanzapine. If the expression level of miR-143-3p is up-regulated, the SZ patient responds to olanzapine.

Preferably, in step 5, the expression level of miRNA is expressed by a $2^{-\Delta Ct}$ cycle value, where $\Delta Ct = (Ct^{miR\text{-}143\text{-}3p\ experimental\ group} - Ct^{u6})$.

Preferably, the miRNA marker miR-143-3p is present in peripheral blood and nerve cells; and when an SZ patient responds to olanzapine, expression levels of the miR-143-3p in peripheral blood and nerve cells are up-regulated.

In a second aspect of the present disclosure, a kit for evaluating a therapeutic effect of olanzapine in the treatment of SZ is provided, including primers for a miRNA marker miR-143-3p and internal reference primers for detecting an expression level of miR-143-3p.

Preferably, the primers for the miRNA marker miR-143-3p include an upstream primer of miR-143-3p, a downstream primer of miR-143-3p, and a stem-loop RT1 primer, where the upstream primer of miR-143-3p has a sequence shown in SEQ ID NO: 1, the downstream primer of miR-143-3p has a sequence shown in SEQ ID NO: 2, and the stem-loop RT1 primer has a sequence shown in SEQ ID NO: 3; and the internal reference primers for detecting the expression level of the miRNA marker miR-143-3p include an internal reference upstream primer, an internal reference downstream primer, and a stem-loop RT2 primer, where an internal reference is U6 RNA, the internal reference upstream primer has a sequence shown in SEQ ID NO: 4, the internal reference downstream primer has a sequence shown in SEQ ID NO: 5, and the stem-loop RT2 primer has a sequence shown in SEQ ID NO: 6.

Preferably, the kit includes the following reagents for a 20 µL PCR system: 10 µL of 2×miRNA L-RT Solution mix, 1.5 µL of miRNA L-RT Enzyme Mix, 4 µg of total RNA, 1 µL of 10 µM Stem-loop primer, and the balance of RNase-Free dd $H_2O$.

The kit detects an expression level of miR-143-3p in a sample to determine whether an SZ patient responds to olanzapine and whether a patient taking olanzapine is at a risk of developing metabolic syndrome. The expression of miR-143-3p in an SZ patient is up-regulated, and the up-regulation of miR-143-3p increases the risk of metabolic syndrome, such as elevated blood sugar level and other side effects.

Preferably, the kit includes the following reagents for a 20 µL PCR system: 10 µL of 2×miRNA L-RT Solution mix, 1.5 µL of miRNA L-RT Enzyme Mix, 4 µg of total RNA, 1 µL of 10 µM Stem-loop primer, and the balance of RNase-Free dd $H_2O$.

In the present disclosure, the term "biomarker" refers to any gene whose expression level in a tissue or cell changes in contrast to its expression level in a normal or healthy cell or tissue.

Those skilled in the art will recognize that the practicability of the present disclosure is not limited to quantifying an expression level of a gene of any particular variant of the marker gene of the present disclosure.

In the present disclosure, the gene expression can be determined by any method known in the art. Those skilled in the art should understand that a means for determining the gene expression is not an important aspect of the present disclosure. An expression level of the biomarker can be detected at a transcriptional level.

Compared with the prior art, the present disclosure has the following beneficial effects.

1. The present disclosure discovers for the first time the differential expression of miR-143-3p in a therapeutic effect of olanzapine in the treatment of SZ, such that an expression level of miR-143-3p can be detected to determine a therapeutic effect of olanzapine in the treatment of SZ.

2. The present disclosure provides a precision medical means for SZ, where a transcriptional level of miR-143-3p is increased in an SZ patient to treat SZ.

3. The present disclosure provides a molecular marker for SZ, and the molecular marker can be used as a detection or treatment index in clinical practice, which provides a theoretical basis for the mechanism research of SZ and the clinical application.

4. The present disclosure provides a diagnostic kit, which provides a basis for early diagnosis of SZ and treatment of SZ with olanzapine.

BRIEF DESCRIPTION OF THE DRAWINGS

Other features, objectives, and advantages of the present disclosure will become more apparent by reading the detailed description of non-limiting examples with reference to the following accompanying drawings.

DETAILED DESCRIPTION OF THE EMBODIMENTS

Figure 1:
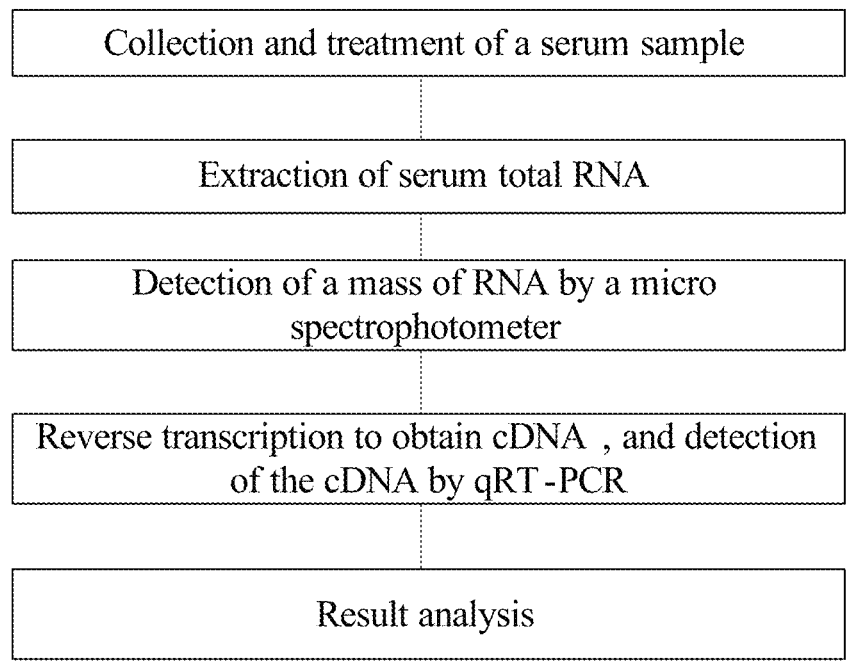
FIG. 1 is a schematic diagram of a method for evaluating a therapeutic effect of olanzapine in the treatment of SZ with a peripheral blood miRNA marker detection kit according to an embodiment of the present disclosure.

The present disclosure is described in detail below with reference to specific examples. The following examples will help those skilled in the art to further understand the present disclosure, but do not limit the present disclosure in any way. It should be noted that several variations and improvements can also be made by a person of ordinary skill in the art without departing from the conception of the present disclosure. These all fall within the protection scope of the present disclosure.

The present disclosure discovers for the first time the differential expression of miR-143-3p in a therapeutic effect of olanzapine in the treatment of SZ, such that an expression level of miR-143-3p can be detected to determine a therapeutic effect of olanzapine in the treatment of SZ.

The technical solutions of the present disclosure are further described in detail below in combination with specific examples.

Example 1 Screening of a miRNA Marker Related to a Therapeutic Effect of Olanzapine in the Treatment of SZ Through High-Throughput Sequencing (HTS)

1. Screening of a miRNA Marker in Peripheral Blood Related to a Therapeutic Effect of Olanzapine in the Treatment of SZ 1.1 Blood was Collected, and a Serum Sample was Prepared Through Centrifugation and then Stored for Later Use.

Peripheral blood was collected from each of 10 SZ patients who did not respond to an olanzapine treatment and 10 SZ patients who responded to an olanzapine treatment, and the patients each signed an informed consent form. The acquisition of all specimens was approved by the Organizational Ethics Committee. 3 mL of fasting venous blood was collected from each of included people in the morning and then immediately centrifuged by a horizontal centrifuge at 2,000 rpm for 8 min to allow serum separation, and a resulting supernatant was placed in a centrifuge tube and then centrifuged at 14,000 rpm and 4° C. for 10 min; and a resulting supernatant was placed in a new centrifuge tube and stored in a −80° C. refrigerator for extraction of total RNA.

1.2 Extraction of Total RNA

A sample was subjected to homogenization with a TRIzol™ reagent, and chloroform was added to make a homogenate separated into a transparent upper aqueous layer (including RNA), an intermediate phase, and a red lower organic layer (including DNA and a protein); RNA was precipitated from the aqueous layer with isopropanol; and the precipitated RNA was washed with ethanol to remove impurities and then resuspended with RNase-free water to obtain total RNA, and the total RNA was stored at −80° C.

1.3 Construction of a miRNA Library

A quality of RNA was tested by the agarose gel electrophoresis technique and AStraGene technique to ensure RNA quality. Specific standards were as follows: The agarose gel electrophoresis technique was used to determine the integrity of RNA and whether there was DNA contamination in RNA; the NanoPhotometer spectrophotometer was used to detect a purity of RNA (OD260/280 and OD260/230 ratios); and the Agilent 2100 bioanalyzer was used to accurately detect the integrity of RNA. When it was detected that the RNA had a complete structure and was not contaminated by DNA, an OD260/280 ratio was 1.8 to 2.0, and an OD260/230 ratio was greater than or equal to 2, the total RNA was considered to be qualified. A T4 RNA ligase 2 (NEB) was used to ligate a linker at a 3' terminus with a small RNA fragment that had a length of 15 nt to 50 nt after being cut (the standard operation steps of NEBNext® Ultra™ RNA Library Prep Kit for Illumina® were adopted); a T4 RNA ligase 1 was used to ligate a linker at a 5' terminus with the small RNA fragment (the standard operation steps of NEBNext® Ultra™ RNA Library Prep Kit for Illumina® were adopted); the ligated RNA fragment was subjected to reverse transcription to obtain cDNA; and a reverse transcription product was amplified by PCR to obtain a cDNA library; and a PCR product of 140 bp to 150 bp was purified by 12% polyacrylamide gel electrophoresis (PAGE) and sequenced subsequently.

1.4 HTS of miRNA and Data Processing

A purified cDNA library was subjected to miRNA HTS and data filtering with a Illumina HiseqXten platform; and miRNA sequencing data were processed with Illumina's Sequencing Control Studio software version 2.8 (SCS v2.8).

2. Screening of a miRNA Marker in NSCs Related to a Therapeutic Effect of Olanzapine in the Treatment of SZ 2.1 Induced Pluripotent Stem Cell (iPSC) Reprogramming Before reprogramming, human PBMCs were transferred to an antibiotic-free fresh medium, pre-warmed in a 37° C. incubator, counted to determine a cell density, and centrifuged at 3,000 rpm and room temperature for 5 min, and a resulting supernatant was discarded; a cell pellet was resuspended with an electroporation buffer to obtain a cell suspension with a cell density of 1.0×104/mL; an appropriate amount of an Episomal iPSC reprogramming vector was added to a Neon Transfection System 100 μL Kit transfection reagent system, and a resulting mixture was gently mixed; the cell suspension was added to the transfection system for electroporation, and a pulsed sample was immediately transferred to a prepared plate with a human embryonic stem cell (hESC) medium; and the plate was placed in an incubator and incubated for about 20 d, and then iPSC clones were observed.

2.2 Directed Differentiation of iPSCs into NSCs

When pluripotent stem cells (PSCs) were obtained, a medium was removed, and a minimum amount of an Accutase solution required to cover a surface of a petri dish was added; the petri dish was incubated at 37° C. for 15 min to 30 min and then observed under a microscope; when all cells were presented as single cells, clones were collected in a fresh hESC medium; cells in the petri dish were ground with a Pasteur pipette and then filtered through a 40 μm cell strainer to remove the debris and cell mass; the cells were washed with 160 g of a hESC medium and centrifuged for 5 min twice to remove the remaining Accutase solution; the cells were resuspended in an ROCK inhibitor-containing hESC medium and coated at a density of greater than 200,000 cells/cm$^2$ on a poly-L-lysine (PLL)-coated Petri dish; the Petri dish was incubated at 37° C. for 30 min in an incubator; non-adherent cells were collected and resuspended in ROCK inhibitor-containing CM; a resulting cell suspension was counted, diluted with ROCK inhibitor-containing CM to an appropriate cell concentration, and coated on a matrigel-coated Petri dish at 10,000 cells/cm$^2$, and the cells were allowed to grow in 10 ng mL-1 FGF-containing CM; when cells began to differentiate, the medium was replaced with a medium including 10 μM SB431542 and 500 ng mL$^{-1}$ KSR; and the medium was changed on day 2, 3, 5, 7, 9, and 11 and was slowly switched from KSR to N$_2$, and cells were observed for 2 weeks to obtain iPSCs-NSCs.

2.3 Extraction of Total RNA

A sample was subjected to homogenization with a TRIzol™ reagent, and chloroform was added to make a homogenate separated into a transparent upper aqueous layer (including RNA), an intermediate phase, and a red lower organic layer (including DNA and a protein); RNA was precipitated from the aqueous layer with isopropanol; and the precipitated RNA was washed with ethanol to remove impurities and then resuspended with RNase-free water to obtain total RNA, and the total RNA was stored at −80° C.

2.4 Construction of a miRNA Library

A quality of RNA was tested by the agarose gel electrophoresis technique and AStraGene technique to ensure RNA quality; a T4 RNA ligase 2 (NEB) was used to ligate a linker at a 3' terminus with a small RNA fragment that had a length of 15 nt to 50 nt after being cut; a T4 RNA ligase 1 was used to ligate a linker at a 5' terminus with the small RNA fragment; the ligated RNA fragment was subjected to reverse transcription to obtain cDNA; and a reverse transcription product was amplified by PCR to obtain a cDNA library; and a PCR product of 140 bp to 150 bp was purified by 12% PAGE and sequenced subsequently.

2.5 HTS of miRNA and Data Processing

A purified cDNA library was subjected to miRNA HTS and data filtering with a Illumina HiseqXten platform; and miRNA sequencing data were processed with Illumina's Sequencing Control Studio software version 2.8 (SCS v2.8).

Result Analysis

Figures 2A, 2B, 2C:
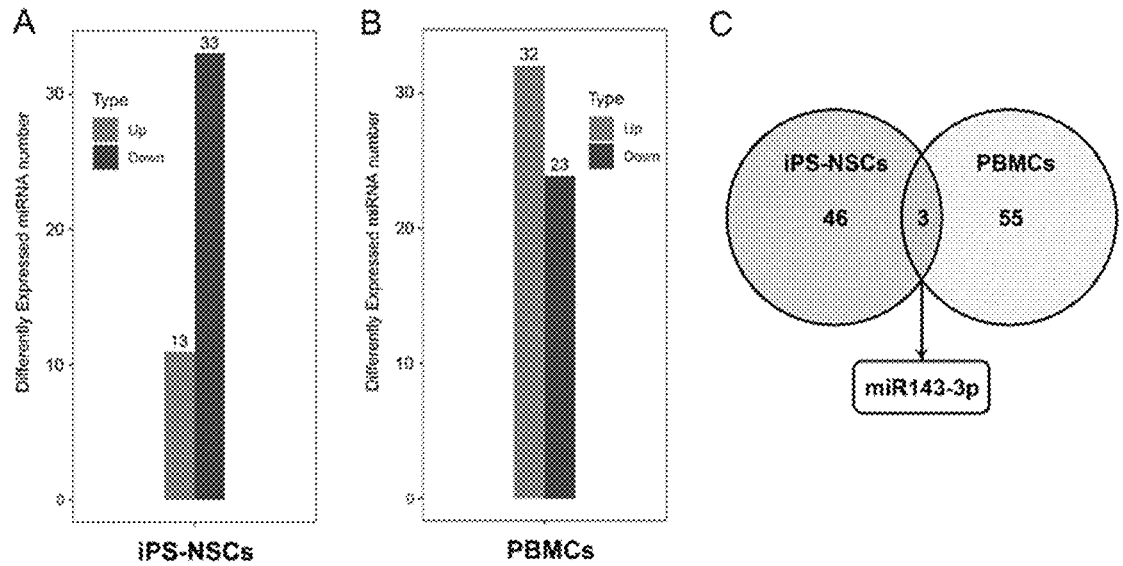
FIGS. 2A-2C show the detection of a gene marker related to a therapeutic effect of olanzapine in the treatment of SZ through miRNA sequencing.

Results were shown in FIGS. 2A-2B. miRNA-seq sequencing results of PBMCs and iPSC-differentiated NSCs showed that 55 and 46 miRNA molecules underwent significant changes (P<0.05) in the patients who did not respond to an olanzapine treatment compared with the patients who responded to an olanzapine treatment, respectively, of which 3 miRNA molecules underwent significant changes in the above two study systems (FIG. 2C). Based on the consistency of significantly changed molecules in the above two study systems and the significance, miR143-3p is likely to be an important biomarker molecule related to a therapeutic effect of olanzapine in the treatment of SZ due to its significant down-regulation in both peripheral blood and NSCs.

Example 2 Verification of Differential Expression of miR-143-3p by qRT-PCR 2.1 Blood was Collected, and a Serum Sample was Prepared Through Centrifugation and then Stored for Later Use.

Peripheral blood was collected from each of 4 of the SZ patients who did not respond to an olanzapine treatment in Example 1 and 4 of the SZ patients who responded to an olanzapine treatment in Example 1, and the remaining operations were the same as in Example 1.

2.2 Extraction of Total RNA

Steps for the extraction of total RNA were the same as in Example 1.

2.3 Detection of a Mass of RNA with an Ultra-Micro Spectrophotometer

2 μL of dissolved RNA was taken, and an absorbance of the dissolved RNA at 260 mm was determined with the ultra-micro spectrophotometer to calculate a yield of RNA.

2.4 Reverse Transcription was Conducted to Obtain cDNA, and the cDNA was Detected Through Fluorescence Quantification.

Primers for the miRNA marker miR-143-3p used in the reverse transcription included an upstream primer of miR-143-3p, a downstream primer of miR-143-3p, and a stem-loop RT1 primer. The upstream primer of miR-143-3p had a sequence shown in SEQ ID NO: 1:

F: CGCGTGAGATGAAGCACTG;

the downstream primer of miR-143-3p had a sequence shown in SEQ ID NO: 2:

R: AGTGCAGGGTCCGAGGTATT; and the stem-loop RT1 primer had a sequence shown in SEQ ID NO: 3:

RT1:
GTCGTATCCAGTGCAGGGTCCGAGGTATTCGCACTGGATACGACGAGCTA.

Internal reference primers for detecting the expression level of the miRNA marker included an internal reference upstream primer, an internal reference downstream primer, and a stem-loop RT2 primer. An internal reference was U6 RNA. The internal reference upstream primer had a sequence shown in SEQ ID NO: 4:

F: AGAGAAGATTAGCATGGCCCCTG;

the internal reference downstream primer had a sequence shown in SEQ ID NO: 5:

R: ATCCAGTGCAGGGTCCGAGG; and the stem-loop RT2 primer had a sequence shown in SEQ ID NO: 6:

RT2:
GTCGTATCCAGTGCAGGGTCCGAGGTATTCGCACTGGATACGACAAAATA.

The reverse transcription was conducted as follows: 2×miRNA L-RT Solution mix was thawed and thoroughly mixed, and miRNA L-RT Enzyme Mix was placed on ice for later use; 10 μL of 2×miRNA L-RT Solution mix, 1.5 μL of miRNA L-RT Enzyme Mix, 4 μg of total RNA, 1 μL of Stem-loop primer (10 μM), and the balance of RNase-Free dd $H_2O$ were added to a reaction tube pre-cooled on ice to obtain a 20 μL reaction system, and a reaction was conducted to obtain cDNA; and the cDNA was detected through fluorescence quantification.

Real-time fluorescence quantitative PCR of miRNA: Operations were conducted according to instructions of the SYBR Green Masrer kit, 3 replicate wells were set for each experiment, and a LightCycler 96 real-time fluorescence quantitative PCR instrument was used for detection.

2.5 Detection Results were Analyzed by a Relative Quantification Method.

The relative quantification method was used for analysis, and an expression level of miRNA was expressed as $2^{-\Delta Ct}$. A $2^{-\Delta Ct}$ cycle value was calculated as follows: $\Delta Ct = (Ct^{miR\text{-}143\text{-}3p\ experimental\ group} - Ct^{u6\ internal\ reference})$. The experiment was completed with 3 replicates. Result data were expressed in the way of mean±standard deviation (SD) and subjected to statistical analysis by SPSS18.0 statistical software. A difference between two was determined by a t test, and it was considered that there was statistical significance when $P<0.05$.

2.6 Result Analysis

Figure 3:
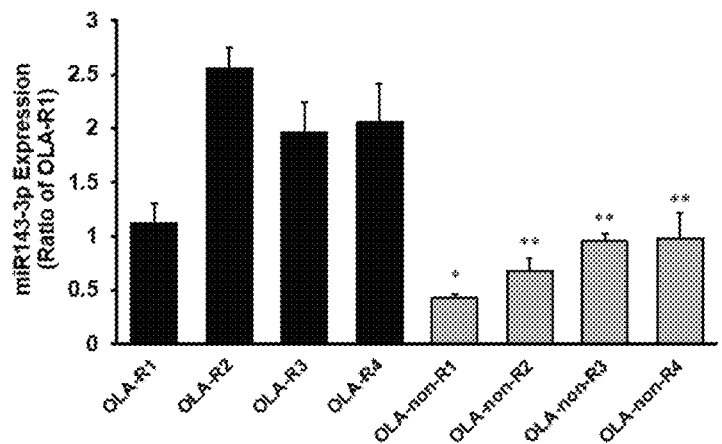
FIG. 3 is a boxplot illustrating the verification of expression of miR-143-3p in neural stem cells (NSCs) of an SZ patient who responds to an olanzapine treatment and an SZ patient who does not respond to an olanzapine treatment by qRT-PCR.
Figure 4:
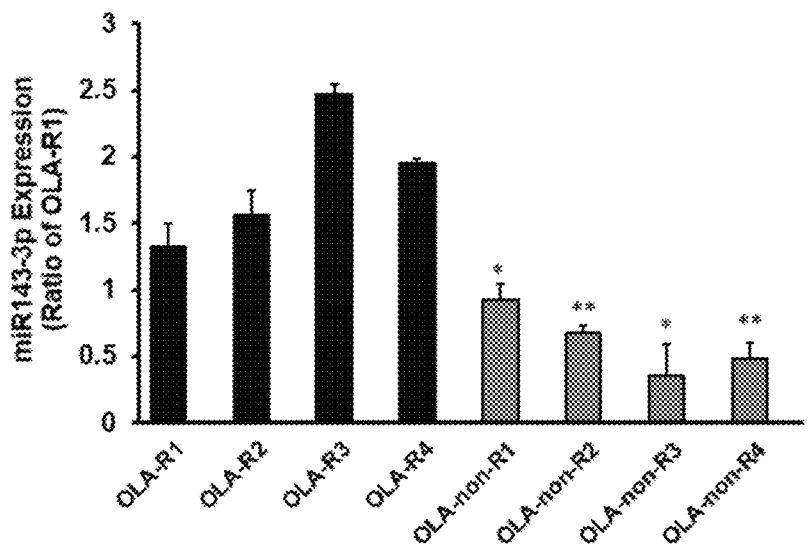
FIG. 4 is a boxplot illustrating the verification of expression of miR-143-3p in peripheral blood mononuclear cells (PBMCs) of an SZ patient who responds to an olanzapine treatment and an SZ patient who does not respond to an olanzapine treatment by qRT-PCR.

RT-PCR test results showed that, compared with the SZ patients who responded to an olanzapine treatment (OLA-R), the expression of the miR-143-3p gene was down-regulated in NSCs (FIG. 3) and PBMCs (FIG. 4) of the SZ patients who did not respond to an olanzapine treatment (OLA-non-R), and the expression level of the miR-143-3p gene was significantly reduced (FIG. 3 and FIG. 4, *$P<0.05$ and **$P<0.01$) with a statistically significant difference ($P<0.05$), which was consistent with the miRNA-seq results in Example 1. It can be seen from the above results that miR143-3p has a consistent expression change trend in human peripheral blood and nerve tissues, and is a candidate molecular marker that can be used to characterize a difference in a therapeutic effect of olanzapine in the treatment of SZ.

Example 3 Study of Differential Expression of the miR-143-3p Gene in Other Nerve Cell Lines 3.1 Cell Cultivation Human neuroblastoma cells (SH-SY5Y cells) were inoculated in a 6-well cell culture plate, an MEM: F12 medium including 10% fetal bovine serum (FBS) was added, and the cells were cultivated in an incubator at 37° C., 5% $CO_2$, and saturated humidity; and cells at a logarithmic growth phase were selected for experiments. When a confluency was about 80%, SH-SY5Y cells were treated with olanzapine at concentrations of 0 μM (control), 1 μM, and 10 μM for 24 h.

3.2 RNA Extraction (1) The medium in the plate was removed, the plate was washed with PBS twice, 1 mL of Trizol was added to each well, the liquid in the plate was pipetted up and down 10 to 15 times, and the plate was allowed to stand at room temperature for 5 min.

(2) A resulting cell suspension was collected in a 1.5 mL enzyme-free EP tube, vortexed for 10 s, and allowed to stand on ice for 5 min; and 200 μL of pre-cooled chloroform was added to each tube, and the tube was shaken manually for 15 s (with a finger against a tube cap) and then allowed to stand at room temperature for 5 min.

(3) The tube was centrifuged at 4° C. and 13,000 rpm for 15 min.

(4) A resulting upper aqueous layer was pipetted to a clean 1.5 mL enzyme-free EP tube (about 400 μL, a middle layer or a lower red liquid layer could not pipetted).

(5) An equal volume of 4° C. pre-cooled isopropanol was added to each tube, and the tube was slowly inverted up and down 10 to 15 times and then allowed to stand at room temperature for 10 min.

(6) The tube was centrifuged at 4° C. and 13,000 rpm for 10 min.

(7) A resulting supernatant was discarded, 1,000 μL of pre-cooled 75% ethanol was added to each tube, and the tube was gently inverted up and down.

(8) The tube was centrifuged at 4° C. and 13,000 rpm for 5 min.

(9) Ethanol was removed, the tube was air-dried at room temperature for less than 10 min until an inner wall of the tube was nearly dry, and 100 μL of RNase-free water was added to each tube for dissolution; and the concentration and purity were determined, and a resulting product was stored at −80° C.

3.3 Detection of a Mass of RNA with an Ultra-Micro Spectrophotometer

Specific steps were the same as in Example 2.

3.4 Reverse Transcription was Conducted to Obtain cDNA, and the cDNA was Detected Through Fluorescence Quantification.

Primers for the miRNA marker miR-143-3p used in the reverse transcription included an upstream primer of miR-143-3p, a downstream primer of miR-143-3p, and a stem-loop RT1 primer. The upstream primer of miR-143-3p had a sequence shown in SEQ ID NO: 1:

F: CGCGTGAGATGAAGCACTG;

the downstream primer of miR-143-3p had a sequence shown in SEQ ID NO: 2:

R: AGTGCAGGGTCCGAGGTATT; and the stem-loop RT1 primer had a sequence shown in SEQ ID NO: 3:

RT1:
GTCGTATCCAGTGCAGGGTCCGAGGTATTCGCACTGGATACGACGAGCTA.

Internal reference primers for detecting the expression level of the miRNA marker included an internal reference upstream primer, an internal reference downstream primer, and a stem-loop RT2 primer. An internal reference was U6 RNA. The internal reference upstream primer had a sequence shown in SEQ ID NO: 4:

F: AGAGAAGATTAGCATGGCCCCTG;

the internal reference downstream primer had a sequence shown in SEQ ID NO: 5:

R: ATCCAGTGCAGGGTCCGAGG; and the stem-loop RT2 primer had a sequence shown in SEQ ID NO: 6:

```
RT2:
GTCGTATCCAGTGCAGGGTCCGAGGTATTCGCACTGGATACGACAAAATA.
```

The reverse transcription was conducted as follows: 2×miRNA L-RT Solution mix was thawed and thoroughly mixed, and miRNA L-RT Enzyme Mix was placed on ice for later use; 10 μL of 2×miRNA L-RT Solution mix, 1.5 μL of miRNA L-RT Enzyme Mix, 4 μg of total RNA, 1 μL of Stem-loop primer (10 μM), and the balance of RNase-Free dd H$_2$O were added to a reaction tube pre-cooled on ice to obtain a 20 μL reaction system, and a reaction was conducted to obtain cDNA; and the cDNA was detected through fluorescence quantification. Real-time fluorescence quantitative PCR of miRNA: Operations were conducted according to instructions of the SYBR Green Master kit, 3 replicate wells were set for each experiment, and a LightCycler 96 real-time fluorescence quantitative PCR instrument was used for detection.

3.5 Detection Results were Analyzed by a Relative Quantification Method.

The relative quantification method was used for analysis, and an expression level of miRNA was expressed as $2^{-\Delta Ct}$. A $2^{-\Delta Ct}$ cycle value was calculated as follows: $\Delta Ct=(Ct^{miR\text{-}143\text{-}3p\ experimental\ group}-Ct^{u6}$ internal reference). The experiment was completed with 3 replicates. Result data were expressed in the way of mean±SD and subjected to statistical analysis by SPSS18.0 statistical software. A difference between two was determined by a t test, and it was considered that there was statistical significance when P<0.05.

3.6 Result Analysis

Figure 5:
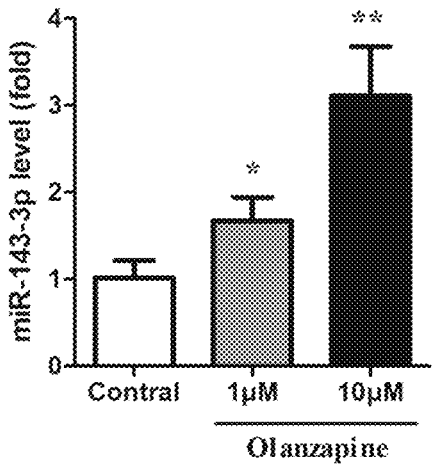
FIG. 5 shows the detection of influence of olanzapine on the expression of miR-143-3p in SH-SY5Y cells by qRT-PCR.

Results were shown in FIG. 5. Compared with the control group (Control), olanzapine at 1 μM and 10 μM significantly increased the expression level of miR-143-3p, and an increased amount of the expression level increased with the increase in dose (FIG. 5, *P<0.05 and **P<0.01). It can be seen from the results that olanzapine at a therapeutic concentration can increase an expression level of miR-143-3p.

The specific examples of the present disclosure are described above. It should be understood that the present disclosure is not limited to the above specific implementations, and a person skilled in the art can make various variations or modifications within the scope of the claims without affecting the essence of the present disclosure. The examples of the present disclosure and features in the examples may be arbitrarily combined with each other in a non-conflicting situation.

What is claimed is:

1. A method for evaluating a therapeutic effect of olanzapine in the treatment of schizophrenia (SZ) in a human patient comprising the following steps:
   detecting an expression level of a microRNA (miRNA) marker miR-143-3p in a SZ patient, wherein detecting the expression level of the miRNA marker miR-143-3p specifically comprises the following steps:
   step 1: collecting blood of a SZ patient and preparing a serum sample through a centrifugation,
   step 2: extracting a total RNA from the serum sample,
   step 3: detecting a total amount of the total RNA with an ultra-micro spectrophotometer, and
   step 4: conducting a reverse transcription to obtain a cDNA, and detecting the cDNA through a fluorescence quantification, wherein
   primers for the miRNA marker miR-143-3p are used in the reverse transcription and the primers for the miR-143-3p comprise:
   an upstream primer of the miRNA marker miR-143-3p having the sequence shown in SEQ ID NO: 1,
   a downstream primer of the miRNA marker miR-143-3p having the sequence shown in SEQ ID NO: 2, and
   a stem-loop RT1 primer having the sequence shown in SEQ ID NO: 3;
   detecting increased expression levels of miRNA marker miR-143-3p in the serum sample as indicative that the SZ patient will be responsive to olanzapine; and
   administering olanzapine to the SZ patient having increased expression levels of the miRNA marker miR-143-3p.

2. The method according to claim 1, wherein in detecting an expression level of miRNA marker miR-143-3p, step 3, an absorbance at 260 mm is determined with the ultra-micro spectrophotometer to calculate the total amount of the total RNA.

3. The method according to claim 1, wherein in detecting an expression level of miRNA marker miR-143-3p, step 4, a relative quantification method comprising internal reference primers is used for calculating the expression level of the miRNA marker miR-143-3p, and the internal reference primers comprise;
   a U6 RNA upstream primer having the sequence shown in SEQ ID NO: 4,
   a U6 RNA downstream primer having the sequence shown in SEQ ID NO: 5, and
   a stem-loop RT2 primer having the sequence shown in SEQ ID NO: 6.

* * * * *

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: The sequence is synthetized.

<400> SEQUENCE: 1
cgcgtgagat gaagcactg                                                19

<210> SEQ ID NO 2
<211> LENGTH: 20
<212> TYPE: DNA
<213> ORGANISM: Artificial Sequence
<220> FEATURE:
<223> OTHER INFORMATION: The sequence is synthetized.

<400> SEQUENCE: 2
agtgcagggt ccgaggtatt                                               20

<210> SEQ ID NO 3
<211> LENGTH: 50
<212> TYPE: DNA
<213> ORGANISM: Artificial Sequence
<220> FEATURE:
<223> OTHER INFORMATION: The sequence is synthetized.

<400> SEQUENCE: 3
gtcgtatcca gtgcagggtc cgaggtattc gcactggata cgacgagcta              50

<210> SEQ ID NO 4
<211> LENGTH: 23
<212> TYPE: DNA
```

```
<213> ORGANISM: Artificial Sequence
<220> FEATURE:
<223> OTHER INFORMATION: The sequence is synthetized.

<400> SEQUENCE: 4
agagaagatt agcatggccc ctg                                           23

<210> SEQ ID NO 5
<211> LENGTH: 20
<212> TYPE: DNA
<213> ORGANISM: Artificial Sequence
<220> FEATURE:
<223> OTHER INFORMATION: The sequence is synthetized.

<400> SEQUENCE: 5
atccagtgca gggtccgagg                                               20

<210> SEQ ID NO 6
<211> LENGTH: 50
<212> TYPE: DNA
<213> ORGANISM: Artificial Sequence
<220> FEATURE:
<223> OTHER INFORMATION: The sequence is synthetized.

<400> SEQUENCE: 6
gtcgtatcca gtgcagggtc cgaggtattc gcactggata cgacaaaata             50
```